US008491625B2

(12) United States Patent
Horner

(10) Patent No.: US 8,491,625 B2
(45) Date of Patent: Jul. 23, 2013

(54) APPARATUS FOR PERFORMING AN ELECTROSURGICAL PROCEDURE

(75) Inventor: Glenn A. Horner, Boulder, CO (US)

(73) Assignee: Covidien LP, Mansfield, MA (US)

( * ) Notice: Subject to any disclaimer, the term of this patent is extended or adjusted under 35 U.S.C. 154(b) by 449 days.

(21) Appl. No.: 12/792,068

(22) Filed: Jun. 2, 2010

(65) Prior Publication Data
US 2011/0301605 A1 Dec. 8, 2011

(51) Int. Cl.
A61B 17/28 (2006.01)
A61B 18/14 (2006.01)

(52) U.S. Cl.
USPC .............................. 606/205; 606/207; 606/51

(58) Field of Classification Search
USPC ...................... 606/51–52, 205–207
See application file for complete search history.

(56) References Cited

U.S. PATENT DOCUMENTS

| D263,020 | S | 2/1982 | Rau, III |
| D295,893 | S | 5/1988 | Sharkany et al. |
| D295,894 | S | 5/1988 | Sharkany et al. |
| 4,829,313 | A | 5/1989 | Taggart |
| 5,250,056 | A | 10/1993 | Hasson |
| D348,930 | S | 7/1994 | Olson |
| 5,383,880 | A | 1/1995 | Hooven |
| 5,389,098 | A | 2/1995 | Tsuruta et al. |
| 5,454,378 | A | 10/1995 | Palmer et al. |
| 5,536,251 | A * | 7/1996 | Evard et al. ............ 604/93.01 |
| 5,540,706 | A | 7/1996 | Aust et al. |
| 5,582,611 | A | 12/1996 | Tsuruta et al. |
| 5,618,307 | A * | 4/1997 | Donlon et al. ............ 606/205 |
| 5,626,607 | A * | 5/1997 | Malecki et al. ............ 606/205 |
| D384,413 | S | 9/1997 | Zlock et al. |
| 5,792,165 | A | 8/1998 | Klieman et al. |
| 5,817,119 | A | 10/1998 | Klieman et al. |
| D424,694 | S | 5/2000 | Tetzlaff et al. |
| D425,201 | S | 5/2000 | Tetzlaff et al. |
| 6,273,887 | B1 | 8/2001 | Yamauchi et al. |
| D449,886 | S | 10/2001 | Tetzlaff et al. |
| D457,958 | S | 5/2002 | Dycus et al. |
| D457,959 | S | 5/2002 | Tetzlaff et al. |

(Continued)

FOREIGN PATENT DOCUMENTS

DE 2415263 10/1975
DE 2514501 10/1976

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

Primary Examiner — Michael Peffley

(57) ABSTRACT

An endoscopic forceps is provided. The endoscopic forceps includes a housing having a shaft that extends therefrom. A rotatable sheath operably couples to the shaft and includes a camming member. A drive assembly includes a drive rod that operably couples to the rotatable sheath. An end effector assembly operatively connected to a distal end of the shaft has a pair of first and second jaw members. One of the first and second jaw members is movable relative to the other jaw member. Actuation of the drive assembly causes the drive rod to rotate within the shaft and rotate the rotatable sheath such that the movable jaw member moves from an initial position to a subsequent position.

20 Claims, 4 Drawing Sheets

U.S. PATENT DOCUMENTS

| | | |
|---|---|---|
| 6,419,675 B1 | 7/2002 | Gallo, Sr. |
| 6,736,813 B2 | 5/2004 | Yamauchi et al. |
| D493,888 S | 8/2004 | Reschke |
| D496,997 S | 10/2004 | Dycus et al. |
| D499,181 S | 11/2004 | Dycus et al. |
| D509,297 S | 9/2005 | Wells |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,540,872 B2 | 6/2009 | Schechter et al. |
| 7,766,910 B2 | 8/2010 | Hixson et al. |
| 7,887,536 B2 | 2/2011 | Johnson et al. |
| 7,918,848 B2 | 4/2011 | Lau et al. |
| 7,951,150 B2 | 5/2011 | Johnson et al. |
| 8,016,827 B2 | 9/2011 | Chojin |
| 8,112,871 B2 | 2/2012 | Brandt et al. |
| 8,114,122 B2 | 2/2012 | Nau, Jr. |
| 8,133,254 B2 | 3/2012 | Dumbauld et al. |
| 8,142,473 B2 | 3/2012 | Cunningham |
| 8,162,965 B2 | 4/2012 | Reschke et al. |
| 8,187,273 B2 | 5/2012 | Kerr et al. |
| 8,197,479 B2 | 6/2012 | Olson et al. |
| 8,226,650 B2 | 7/2012 | Kerr |
| 8,251,994 B2 | 8/2012 | McKenna et al. |
| 8,266,783 B2 | 9/2012 | Brandt et al. |
| 8,277,446 B2 | 10/2012 | Heard |
| 8,277,447 B2 | 10/2012 | Garrison et al. |
| 8,287,536 B2 | 10/2012 | Mueller et al. |
| 8,292,886 B2 | 10/2012 | Kerr et al. |
| 8,323,310 B2 | 12/2012 | Kingsley |
| 2006/0064085 A1 | 3/2006 | Schechter et al. |
| 2007/0260242 A1 | 11/2007 | Dycus et al. |
| 2009/0018535 A1 | 1/2009 | Schechter et al. |
| 2010/0023009 A1 | 1/2010 | Moses et al. |
| 2010/0087816 A1 | 4/2010 | Roy |
| 2010/0094271 A1 | 4/2010 | Ward et al. |
| 2010/0094287 A1 | 4/2010 | Cunningham |
| 2010/0100122 A1 | 4/2010 | Hinton |
| 2010/0130971 A1 | 5/2010 | Baily |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0249769 A1 | 9/2010 | Nau, Jr. et al. |
| 2010/0280511 A1 | 11/2010 | Rachlin et al. |
| 2011/0015632 A1 | 1/2011 | Artale |
| 2011/0034918 A1 | 2/2011 | Reschke |
| 2011/0046623 A1 | 2/2011 | Reschke |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0082494 A1 | 4/2011 | Kerr et al. |
| 2011/0087221 A1 | 4/2011 | Siebrecht et al. |
| 2011/0098689 A1 | 4/2011 | Nau, Jr. et al. |
| 2011/0118736 A1 | 5/2011 | Harper et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 20121161 | 4/2002 |
| DE | 10045375 | 10/2002 |
| DE | 20 2007 009317 | 10/2007 |
| DE | 19738457 | 1/2009 |
| EP | 1159926 | 12/2001 |
| EP | 1177771 | 2/2002 |
| EP | 1777771 | 2/2002 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 99/03407 | 1/1999 |
| WO | WO 99/03408 | 1/1999 |
| WO | WO 99/03409 | 1/1999 |
| WO | WO 00/36986 | 6/2000 |
| WO | WO 01/54604 | 8/2001 |
| WO | WO 2005/110264 | 11/2005 |
| WO | WO 2008045348 | 4/2008 |
| WO | WO 2009/039510 | 3/2009 |
| WO | WO 2009039179 | 3/2009 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967, British Medical Journal Feb. 6, 1976, vol. 1, nr. 5431 p. 361, ISSN: 0007-1447.

Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5. dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8, dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.

Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10,,2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report EP11168419.7 dated Aug. 8, 2011.
International Search Report EP11168419.7 dated Oct. 11, 2011.
International Search Report EP11168455.1 dated Sep. 26, 2011.
U.S. Appl. No. 12/336,970, filed Dec. 17, 2008, Sremcich et al.
European Search Report corresponding to EP 12169753.6, dated Sep. 14, 2012.
European Search Report corresponding to EP 11168458.5, dated Jul. 21, 2011.

* cited by examiner

APPARATUS FOR PERFORMING AN ELECTROSURGICAL PROCEDURE

BACKGROUND

1. Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

An increased mechanical advantage and/or mechanical efficiency with respect to transferring the closure force(s) from the handle assembly to the jaw members may prove advantageous in the relevant art.

SUMMARY

The present disclosure provides an endoscopic forceps. The endoscopic forceps includes a housing having a shaft that extends therefrom that defines a longitudinal axis therethrough. A rotatable sheath is operably coupled to the shaft and includes a camming member. A drive assembly includes a drive rod that operably couples to the rotatable sheath. An end effector assembly operatively connects to a distal end of the shaft and has a pair of first and second jaw members. One or both of the first and second jaw members is movable relative to the other jaw member from an initial position wherein the first and second jaw members are disposed in spaced relation relative to one another, to a subsequent position wherein the first and second jaw members cooperate to grasp tissue therebetween. Actuation of the drive assembly causes the drive rod to rotate within the shaft and rotate the rotatable sheath such that the movable jaw member moves from the initial position to the subsequent position.

The present disclosure provides an endoscopic forceps. The endoscopic forceps includes a housing having a shaft that extends therefrom that defines a longitudinal axis therethrough. A rotatable sheath includes a camming member and is movable relative to the shaft. A drive assembly includes a drive rod that is rotatable relative to the shaft and is in operative communication with the rotatable sheath for imparting rotational movement thereof. An end effector assembly operatively connects to a distal end of the shaft and has a pair of first and second jaw members. One or both of the first and second jaw members is movable relative to the other jaw member from an initial position wherein the first and second jaw members are disposed in spaced relation relative to one another, to a subsequent position wherein the first and second jaw members cooperate to grasp tissue therebetween. Actuation of the drive assembly causes the rotatable sheath to move the movable jaw member from the initial position to the subsequent position.

In certain embodiments, a plurality of non-conductive stop members may be disposed on an inner facing surface of at least one of the first and second jaw members. The stop members are configured to maintain a uniform distance between the jaw members along the length thereof.

BRIEF DESCRIPTION OF THE DRAWING

Various embodiments of the present disclosure are described hereinbelow with references to the drawings, wherein.

DETAILED DESCRIPTION

Figure 1A:
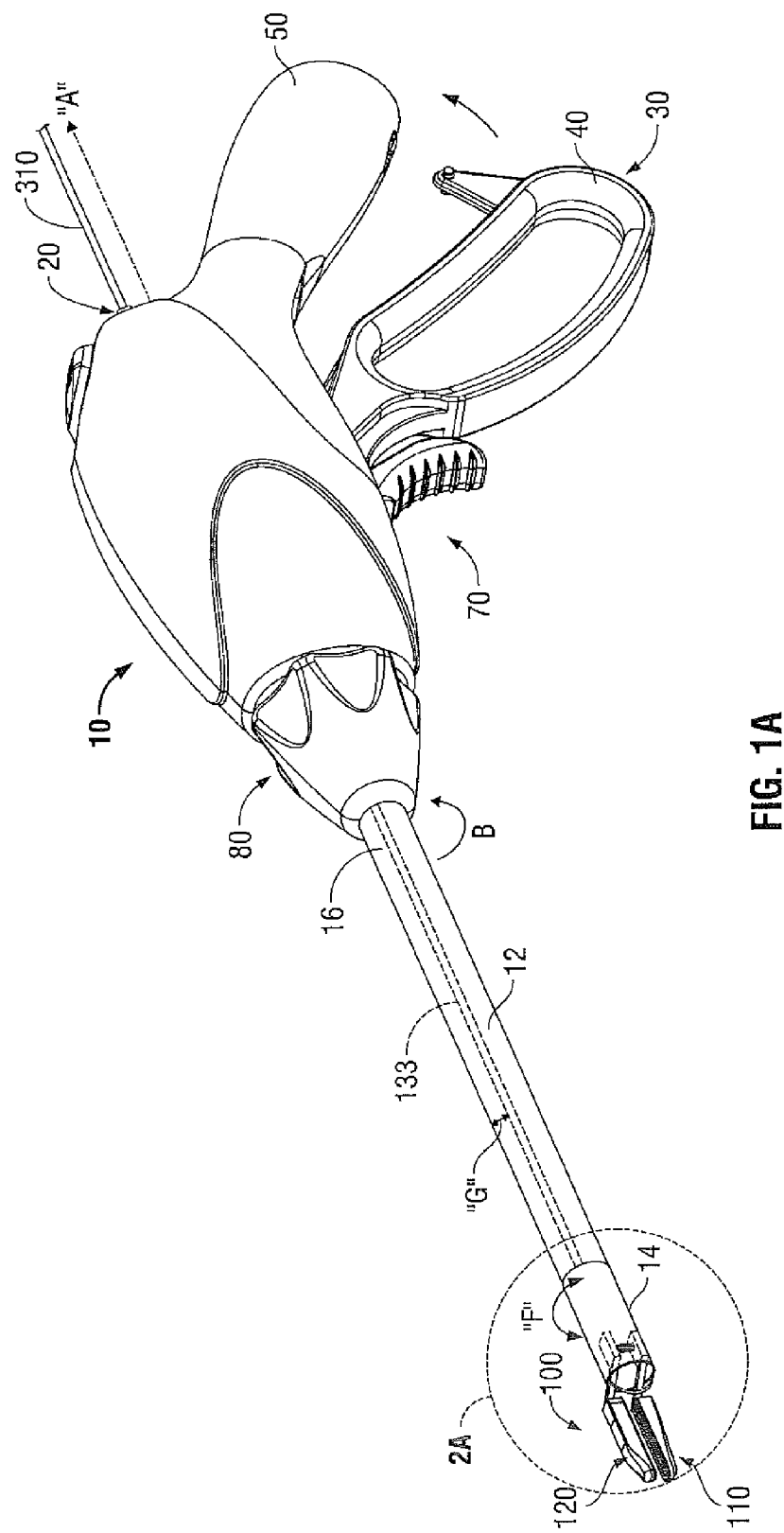
FIG. 1A is a side, perspective view of an endoscopic bipolar forceps showing an end effector assembly including jaw members in an open configuration according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to the end which is closer to the user, while the term "distal" will refer to the end that is farther from the user.

Figure 1B:
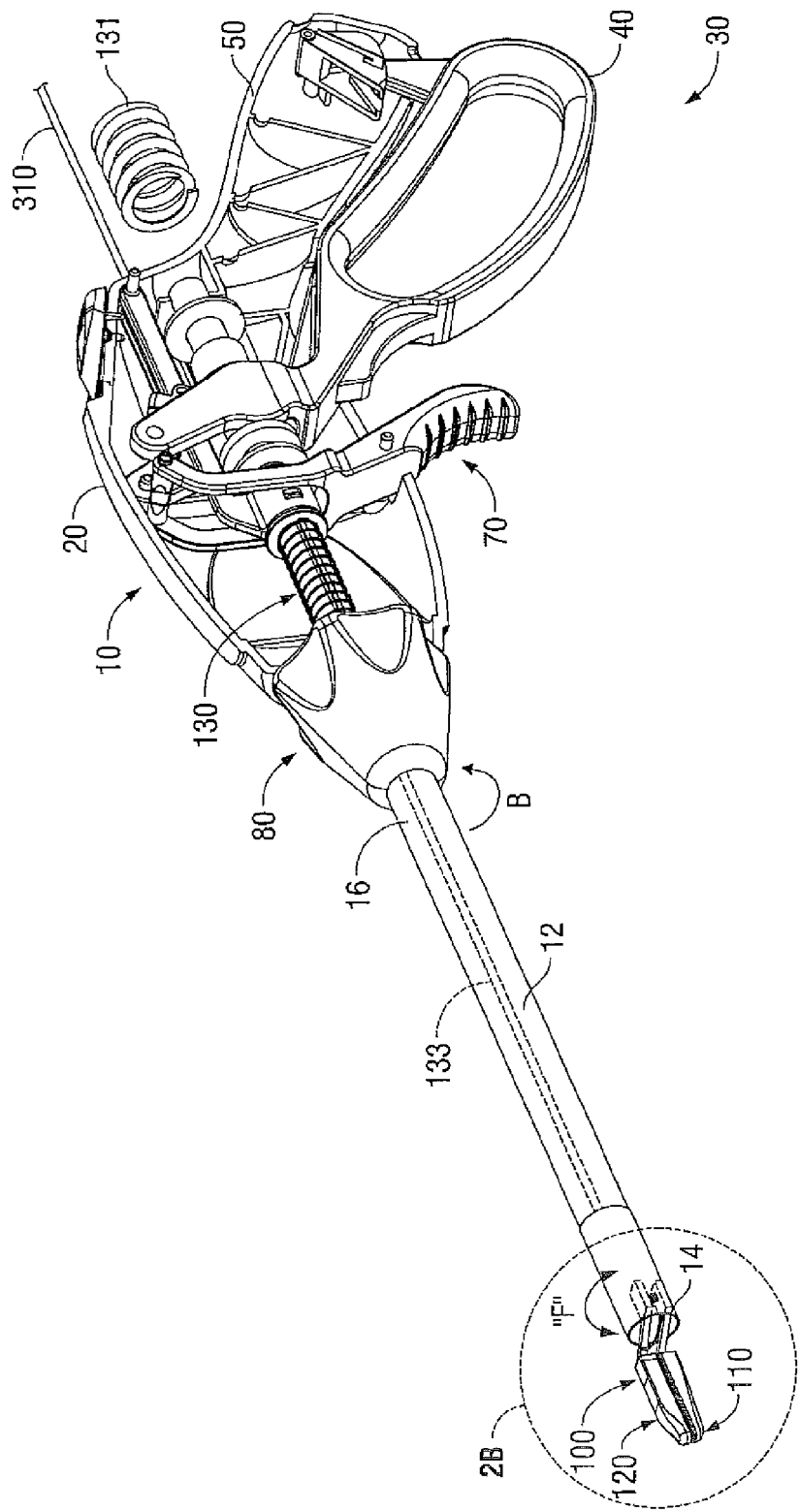
FIG. 1B is a side, perspective view of the endoscopic bipolar forceps depicted in FIG. 1A illustrating internal components of a handle assembly associated with the endoscopic bipolar forceps and the jaw members in a closed configuration.

With reference to FIGS. 1A and 1B, an illustrative embodiment of an electrosurgical apparatus, e.g., a bipolar forceps 10 is shown. Bipolar forceps 10 (forceps 10) is operatively and selectively coupled to an electrosurgical generator (not shown) for performing an electrosurgical procedure. As noted above, an electrosurgical procedure may include sealing, cutting, cauterizing, coagulating, desiccating, and fulgurating tissue all of which may employ RF energy. The generator may be configured for monopolar and/or bipolar modes of operation. The generator may include or is in operative communication with a system (not shown) that may include one or more processors in operative communication with one or more control modules that are executable on the processor. The control module (not shown) may be configured to instruct one or more modules to transmit electrosurgical energy, which may be in the form of a wave or signal/pulse, via one or more cables (e.g., an electrosurgical cable 310) to the forceps 10.

Forceps 10 is shown configured for use with various electrosurgical procedures and generally includes a housing 20, electrosurgical cable 310 that connects the forceps 10 to the source of electrosurgical energy (e.g., the electrosurgical generator), a handle assembly 30, a rotating assembly 80, a trigger assembly 70, and an end effector assembly 100 that operatively connects to a shaft 12 associated with the forceps 10. End effector assembly 100 includes opposing jaw members 110 and 120 (FIGS. 1A and 1B) that mutually cooperate to grasp, seal and, in some cases, divide large tubular vessels and large vascular tissues. In the illustrated embodiment, one of the jaw members, e.g., jaw member 120, is movable, and one of the jaw members, e.g., jaw member 110, is stationary, described in greater detail below. In other embodiments, both of the jaw members 110, 120 are movable.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is ultimately connected to a rotatable sheath 17 that is operably coupled to a distal end 14 of the shaft 12, which together mechanically cooperate to impart movement of the movable jaw member, e.g., jaw member 120, to move from an open or initial position, wherein the jaw members 110 and 120 are disposed in spaced relation relative to one another, to a subsequent or clamping (or closed) position, wherein the jaw members 110 and 120 cooperate to grasp tissue therebetween.

For a more detailed description of the forceps 10 including handle assembly 30 including movable handle 40, rotating assembly 80, trigger assembly 70, and electrosurgical cable 310 (including line-feed configurations and/or connections), reference is made to commonly owned U.S. patent application Ser. No. 11/595,194 filed on Nov. 9, 2006.

As noted above, conventional drive assemblies typically utilize one or more types of springs, e.g., a compression spring, to facilitate closing the jaw members 110 and 120. For illustrative purposes, a compression spring 131 is shown separated from the housing 20 (FIG. 1B). In accordance with the present disclosure, a drive assembly 130 includes a drive rod 133 that is in operative communication with rotatable sheath 17 to impart movement of the movable jaw member, e.g., jaw member 120. Accordingly, the need for a spring 131 operably positioned within the housing 20 is eliminated.

Continuing with reference to FIGS. 1A and 1B, drive assembly 130 is in operative communication with the movable handle 40 via one or more suitable mechanical interfaces, e.g., linkage configuration, gear configuration, or combination thereof. The drive rod 133 operably couples to the rotatable sheath 17 via one or more suitable coupling methods, e.g., soldering, brazing, or welding. Drive rod 133 is configured such that proximal movement of the movable handle 40 causes the drive rod 133 to rotate within an interior of the shaft 12 in a direction indicated by directional arrow "G", e.g., a clockwise direction, such that the rotatable sheath 17 rotates toward the movable jaw member, e.g., jaw member 120, see FIGS. 1A and 2A-2B, for example.

Figure 2A:
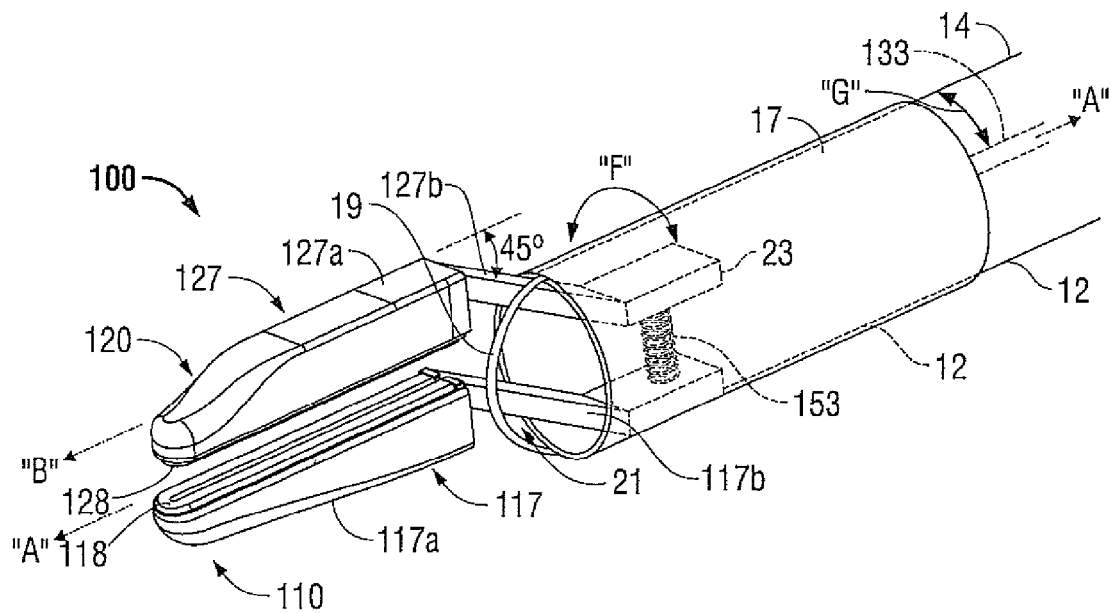
FIG. 2A is an enlarged view of the area of detail depicted in FIG. 1A.

Shaft 12 includes distal end 14 that is configured to mechanically engage the end effector assembly 100 and a proximal end 16 that is configured to mechanically engage the housing 20 (FIGS. 1A-2). In the illustrated embodiment, distal end 14 extends within and along an interior of the rotatable sheath 17, FIG. 2A for example.

A support structure 15 of suitable dimensions is operably disposed on an internal frame of the distal end 14 of the shaft 12 and operably couples to the end effector 100. More particularly, the support structure 15 operably couples to one of the jaw members, e.g., jaw member 110. Support structure 15 is disposed in a substantially fixed or non-movable orientation with respect to the rotatable sheath 17.

Rotatable sheath 17 is configured to rotate, e.g., in either a clockwise or counter-clockwise direction (indicated by directional arrow "F"). In the illustrated embodiment, rotatable sheath 17 is operably coupled to movable handle 40 via drive rod 133 such that actuation of the movable handle 40 causes the rotatable sheath 17 to rotate relative to the end effector 100 including the jaw members 110 and 120. Alternatively, the rotatable sheath 17 and/or shaft 12 may be configured to rotate without the use of the movable handle 40. In this instance, a user may grasp rotatable sheath 17 and/or shaft 12 and physically or manually rotate the rotatable sheath 17 and/or shaft 12 relative to the end effector 100 including the jaw members 110 and 120. In either instance, rotation of the rotatable sheath 17 in the counter-clockwise direction causes the movable jaw member, e.g., jaw member 120, to rotate toward or "fold" onto the stationary jaw member, e.g., jaw member 110, see FIG. 2A in combination with FIG. 2B.

A camming member 19 is operably coupled to the rotatable sheath 17 and is configured to impart movement of the movable jaw member, e.g., jaw member 120, when the rotatable sheath 17 is rotated, i.e., when the movable handle 40 is moved proximally. To this end, camming member 19 is movable from an initial position, wherein the camming member 19 is in a substantially parallel orientation (see FIGS. 1A and 2A) with respect to the longitudinal axis "A-A," to final position, wherein the camming member 19 is disposed in a generally oblique orientation (see FIGS. 1B and 2B) with respect to the longitudinal axis "A-A." In the illustrated embodiment, when the camming member 19 is in the initial position, the jaw members 110 and 120 are in the open configuration and the movable handle 40 is in a distal most position, and when the camming member 19 is in the final position, the jaw members 110 and 120 are in the closed configuration and the movable handle 40 is in a proximal most position (see FIGS. 1A-1B).

Movable handle 40 and rotatable sheath 17 including camming member 19 are configured to provide the necessary closure force on the jaw members 110 and 120 for sealing tissue, e.g., in the range of about 3 kg/cm$^2$ to about 16 kg/cm$^2$, when the camming member 19 is fully rotated (i.e., in the final position) and the jaw members 110, 120 are in the closed position. To this end, camming member 19 may have any suitable configuration. In the illustrated embodiment, the camming member 19 includes a generally circumferential, "loop-like" configuration that defines an opening 21 of suitable proportion. Camming member 19 extends past a distal end of the rotatable sheath 17. More particularly, the camming member 19 extends past the distal end of the rotatable sheath 17 and is disposed adjacent a proximal portion 117b and 127b of the respective jaw members 110 and 120, see FIGS. 2A and 2B. Accordingly, when the rotatable sheath 17 including camming member 19 is rotated, the camming member 19 contacts a proximal end, e.g., a proximal end 127b, or portion thereof, of a respective jaw housing, e.g., a jaw housing 127.

In certain embodiments, a suitable locking device (not shown) may be operably associated with the rotatable sheath 17, camming member 19 and/or shaft 12 and may be configured to lock the rotatable sheath 17 and/or camming member 19 in one or more positions, e.g., a position that corresponds to the clamping position of the jaw members 110 and 120. For example, a ratchet/pawl assembly may be utilized.

Figure 2B:
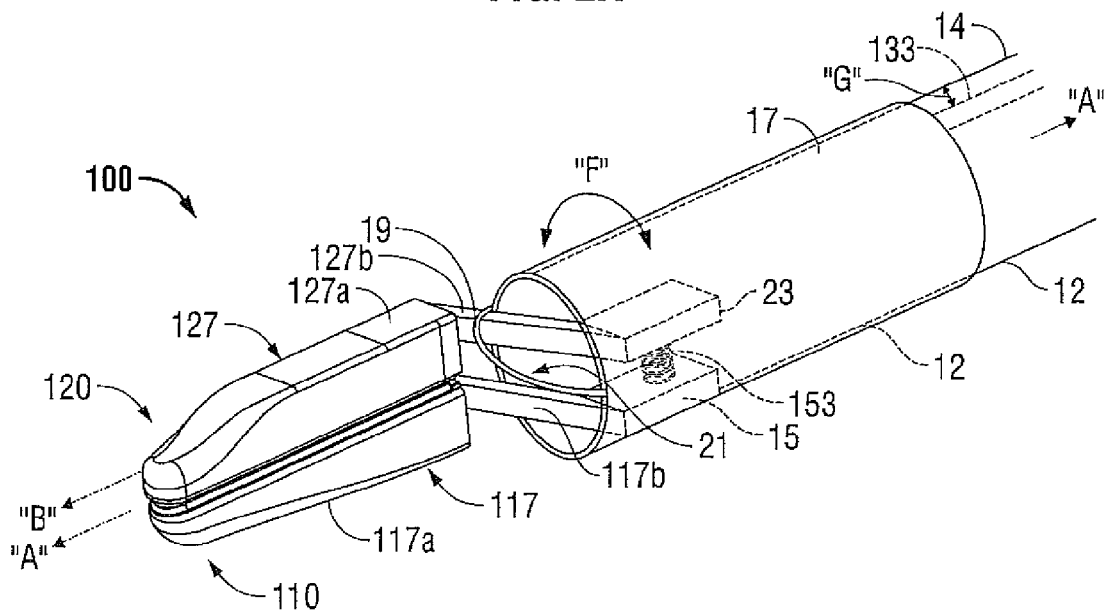
FIG. 2B is an enlarged view of the area of detail depicted in FIG. 1B.

With reference to FIGS. 2A and 2B, jaw members 110, 120 are operatively coupled to each other and disposed adjacent the distal end 14 of shaft 12. In the illustrated embodiment, jaw member 110 is illustrated as being the stationary jaw member and jaw member 120 is illustrated as being the movable jaw member. As can be appreciated, this configuration of the jaw members 110 and 120 may be reversed as needed during the manufacture process. Respective electrically conductive seal plates 118 and 128 are operably supported on and secured to proximal ends 117a and 127a of respective jaw housings 117 and 127 of respective the jaw members 110 and 120.

Jaw members 110 and 120 are substantially identical to each other. In view thereof, the operative components associated with the jaw housing 117 are described in further detail with respect to jaw member 110, and only those features distinct to jaw member 120 and jaw housing 127 will be described hereinafter.

Jaw housing 117, and operative components associated therewith, may be formed from any suitable material, including but not limited to metal, metal alloys, plastic, plastic composites, etc. In the illustrated embodiment, jaw member 110 is formed from metal.

Proximal end 117b of the jaw member 110 operably couples to the support structure 15 of the shaft 12. More particularly, proximal end 117b is fixedly coupled to the support structure 15 by known coupling methods. In the illustrated embodiment, the proximal end 1176 is spot welded to the support structure 15.

Proximal end 117b of the jaw housing 117 extends distally past the rotatable sheath 17. More particularly, proximal end 117b extends out of the rotatable sheath 17 and is disposed in an "offset" or oblique orientation with respect to an axis "B-B" that is defined through the jaw members 110 and 120. Axis "B-B" is disposed in a parallel orientation with respect to the longitudinal axis "A-A" that is defined through the shaft 12 (see FIGS. 2A and 2B). Proximal end 117b may be disposed at any suitable angle, e.g., 0-90°, with respect to the axis "B-B" or the longitudinal axis "A-A." In the illustrated embodiment, proximal end 1176 is oriented at approximately a 45° angle with respect to the axis "B-B." For illustrated purposes, the 45° angle is shown with respect to proximal end 127b of jaw housing 127. Disposing the proximal end 117b in an oblique orientation with respect to the axis "B-B" facilitates opening and closing the jaw members 110 and 120. (please confirm)

A distinguishing feature of the jaw member 120 when compared to jaw member 110 is that jaw member 120 is movable with respect to jaw member 110. To this end, proximal end 127b is configured to contact camming member 19 when the rotatable sheath 17 is rotated. Proximal end 127b operably couples to or includes a movable support structure 23 that is operably coupled to one or more suitable springs 153, e.g., a compression spring, (one spring shown in the representative drawings). Support structure 23 moves against the bias of spring 153 in a direction that is orthogonal to the longitudinal axes "A-A" and "B-B." Disposing the support structure 23 orthogonal with respect to the longitudinal axes "A-A" and "B-B" facilitates moving the movable jaw member, e.g., jaw member 120, from the initial position to the subsequent position.

Compression spring 153 is operably disposed between support structures 15 and 23. More particularly, spring 153 (or other suitable spring) is operably coupled (by suitable coupling methods, e.g., injection molding) to the support structures 15 and 23 associated with respective jaw members 110 and 120 and biases jaw member 120 in the open configuration, see FIG. 2A.

In use, initially jaw member 120 is biased in an opened position (FIGS. 1A and 2A). Tissue is positioned between the jaw members 110 and 120. Movable handle 40 is moved proximally causing the rotatable sheath 17 including the camming member 19 to rotate, e.g., rotate in a counter-clockwise direction. Rotating the camming member 19 in the counter-clockwise direction results in the camming member 19 contacting the proximal end 127b of the jaw member 120, which, in turn, causes jaw member 120 to move toward or "fold" onto jaw member 110 (FIGS. 1B and 2B) such that tissue is grasped between the jaw members 110 and 120. The combination of movable handle 40, drive rod 133 and rotatable sheath 17 including camming member 19 is configured such that when the camming member 19 is fully rotated and in the closed or clamping position, the jaw members 110, 120 generate the necessary sealing or closure force, e.g., in the range of about 3 kg/cm$^2$ to about 16 kg/cm$^2$, on the tissue disposed therebetween. In addition, an additional mechanical advantage at the jaws 110 and 120 is provided and reduces the frictional losses that are typically associated with conventional forceps when a drive rod is translated within a shaft to make the necessary closure force to seal tissue, e.g., the closure force is offloaded and/or diminished by rotation of the rotatable sheath 17 including the camming member 19.

From the foregoing and with reference to the various figure drawings, those skilled in the art will appreciate that certain modifications can also be made to the present disclosure without departing from the scope of the same. For example, other spring mechanisms such as, for example, foam, spring washers, bellows and so forth, may be operably associated with support structures 15 and 23, and utilized to generate a closure or sealing force at the jaw members.

Although the movable jaw member 120 has been described as being coupled to the support structure 23, it is within the purview of the present disclosure that the movable jaw member 120 may be directly coupled to the rotatable sheath 17. More particularly, a portion, e.g., proximal end 127b, of the jaw housing 127, may be coupled to the rotatable sheath 17. In this instance, jaw member 120 is configured to move simultaneously or in unison with the rotatable sheath 17. Accordingly, and in this instance, the need for the camming member 19 and/or spring 153 is eliminated.

Figure 3:
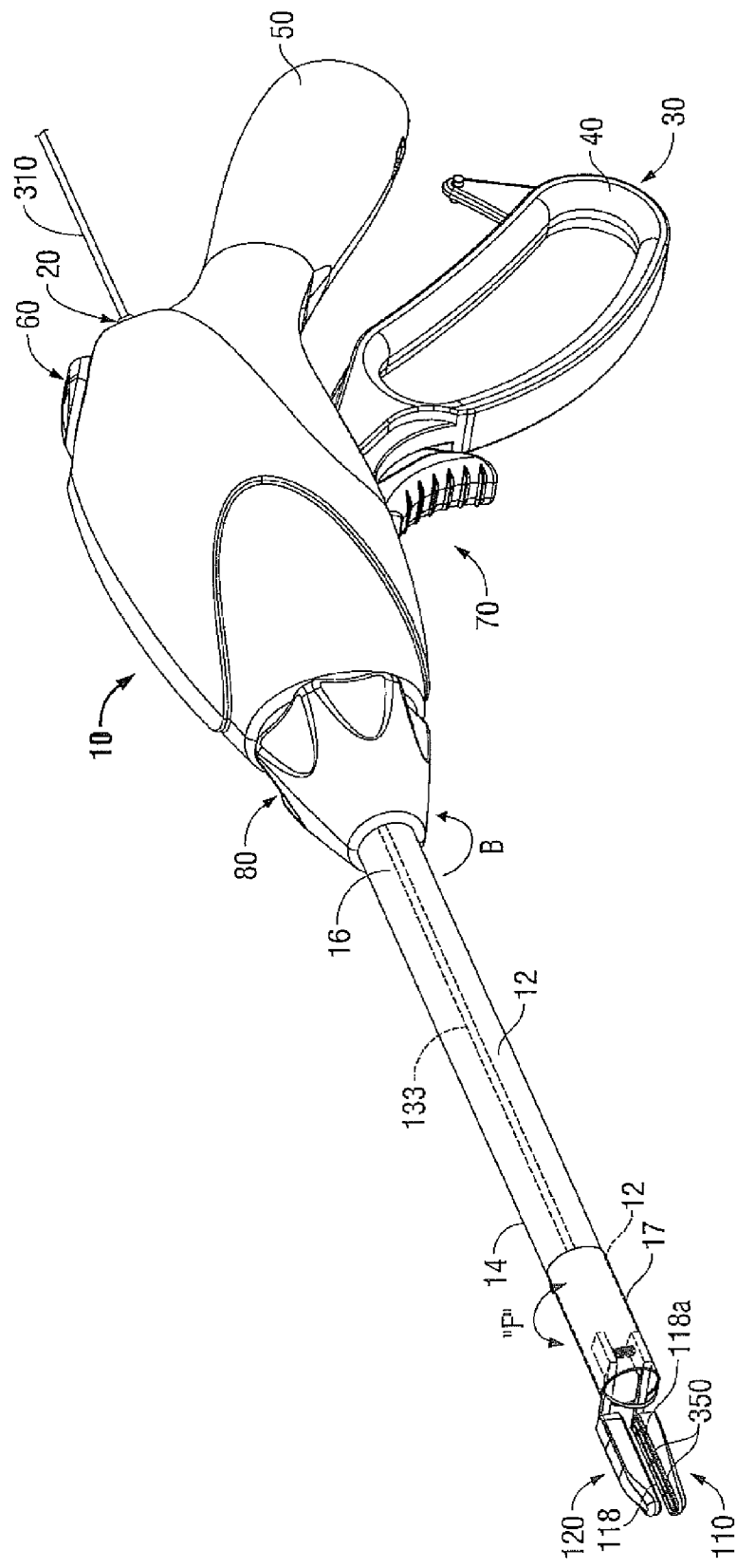
FIG. 3 is a side, perspective view of an endoscopic bipolar forceps showing an end effector assembly including jaw

As best seen in FIG. 3, in order to achieve a desired spacing between the electrically conductive surfaces of the respective jaw members 110 and 120, (i.e., gap distance) and apply a desired force to seal the tissue, one or both of the jaw member 110 and/or 120 may include one or more stop members 350 that limits the movement of the two opposing jaw members 110 and 120 relative to one another. The stop member 350 may be disposed on an inner facing surface of one or both of the jaw members 110 and 120. More particularly, stop member 350 extends from a seal surface 118a of seal plate 118 a predetermined distance according to the specific material properties (e.g., compressive strength, thermal expansion, etc.) to yield a consistent and accurate gap distance during sealing. In the illustrated embodiment, the stop members extend from the seal surface 118a a distance that ranges from about 0.001 inches to about 0.006 inches. The gap distance between opposing sealing surface 118a and a an opposing seal surface (not explicitly shown) of the seal plate 128 during sealing ranges from about 0.001 inches to about 0.006 inches and, preferably, between about 0.002 and about 0.003 inches. The configuration of a seal surface 118a with stop members 350 facilitates in maintaining a uniform distance between the jaw members 110 and 120 along the length thereof during tissue sealing.

For a more detailed description of the stop members 350 and operative components associated therewith, reference is made to commonly-owned U.S. patent application Ser. No. 12/348,748 filed Jan. 5, 2009.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
 a housing having a shaft that extends therefrom that defines a longitudinal axis therethrough;
 a rotatable sheath operably coupled to the shaft, the rotatable sheath including a camming member;
 a drive assembly including a drive rod that operably couples to the rotatable sheath; and
 an end effector assembly operatively connected to a distal end of the shaft and having a pair of first and second jaw members, at least one of the first and second jaw members movable relative to the other jaw member from an initial position wherein the first and second jaw members are disposed in spaced relation relative to one another, to a subsequent position wherein the first and second jaw members cooperate to grasp tissue therebetween,
 wherein actuation of the drive assembly causes the drive rod to rotate within the shaft and rotate the rotatable sheath such that the at least one movable jaw member moves from the initial position to the subsequent position.

2. An endoscopic forceps according to claim 1, wherein the first and second jaw members are offset relative to the longitudinal axis such that rotation of the rotatable sheath causes the camming member to contact the at least one movable jaw member.

3. An endoscopic forceps according to claim 1, wherein the camming member includes a general loop-like configuration.

4. An endoscopic forceps according to claim 1, wherein a spring is operably associated with the first and second jaw members and is configured to bias the movable jaw member in the initial position.

5. An endoscopic forceps according to claim 4, wherein the spring operably couples to a support structure that is operably disposed on the shaft and a support structure that is operably coupled to the at least one moveable jaw member.

6. An endoscopic forceps according to claim 5, wherein a proximal end of the stationary jaw member operably couples to the support structure operably disposed on the shaft.

7. An endoscopic forceps according to claim 1, wherein the rotatable sheath is operably coupled to a distal end of the shaft.

8. An endoscopic forceps according to claim 1, wherein a movable handle operably associated with the drive assembly is configured to actuate the drive rod when the movable handle is moved proximally.

9. An endoscopic forceps according to claim 1, wherein the camming member extends past a distal end of the rotatable sheath and is disposed adjacent a proximal end and of a respective jaw member.

10. An endoscopic forceps according to claim 4, wherein when the at least one movable jaw member is moved to the subsequent position, the combination of the camming member and the spring generate a closure force that ranges from about 3 kg/cm$^2$ to about 16 kg/cm$^2$ between the first and second jaw members for sealing tissue.

11. An endoscopic forceps, comprising:
 a housing having a shaft that extends therefrom that defines a longitudinal axis therethrough;
 a rotatable sheath including a camming member, the rotatable sheath movable relative to the shaft;
 a drive assembly including a drive rod rotatable relative to the shaft and in operative communication with the rotatable sheath for imparting rotational movement thereof; and
 an end effector assembly operatively connected to a distal end of the shaft and having a pair of first and second jaw members, at least one of the first and second jaw members movable relative to the other jaw member from an initial position wherein the first and second jaw members are disposed in spaced relation relative to one another, to a subsequent position wherein the first and second jaw members cooperate to grasp tissue therebetween,
 wherein actuation of the drive assembly causes the rotatable sheath to move the at least one movable jaw member from the initial position to the subsequent position.

12. An endoscopic forceps according to claim 11, wherein the first and second jaw members are offset relative to the longitudinal axis such that rotation of the rotatable sheath causes the camming member to contact the at least one movable jaw member.

13. An endoscopic forceps according to claim 11, wherein the camming member includes a general loop-like configuration.

14. An endoscopic forceps according to claim 11, wherein a spring is operably associated with the first and second jaw members and is configured to bias the movable jaw member in the initial position, the spring operably coupled to a support structure that is operably disposed on the shaft and a support structure that is operably coupled to the at least one moveable jaw member.

15. An endoscopic forceps according to claim 11, wherein the rotatable sheath is operably coupled to a distal end of the shaft.

16. An endoscopic forceps according to claim 11, wherein a movable handle operably associated with the drive assembly is configured to actuate the drive rod when the movable handle is moved proximally.

17. An endoscopic forceps according to claim 11, wherein the camming member extends past a distal end of the rotatable sheath and is disposed adjacent a proximal end and of a respective jaw member.

18. An endoscopic forceps according to claim 11, wherein when the at least one movable jaw member is moved to the subsequent position, the combination of the camming member and the spring generate a closure force that ranges from about 3 kg/cm$^2$ to about 16 kg/cm$^2$ between the first and second jaw members for sealing tissue.

19. An endoscopic forceps, comprising:
   a housing having a shaft that extends therefrom that defines a longitudinal axis therethrough;
   a rotatable sheath operably coupled to the shaft, the rotatable sheath including a camming member;
   a drive assembly including a drive rod that operably couples to the rotatable sheath;
   an end effector assembly operatively connected to a distal end of the shaft and having a pair of first and second jaw members, at least one of the first and second jaw members movable relative to the other jaw member from an initial position wherein the first and second jaw members are disposed in spaced relation relative to one another, to a subsequent position wherein the first and second jaw members cooperate to grasp tissue therebetween;
   a plurality of non-conductive stop members disposed on an inner facing surface of at least one of the first and second jaw members, the stop members configured to maintain a uniform distance between the jaw members along the length thereof,
   wherein actuation of the drive assembly causes the drive rod to rotate within the shaft and rotate the rotatable sheath such that the at least one movable jaw member moves from the initial position to the subsequent position.

20. An endoscopic forceps according to claim 18, wherein the plurality of stop members extend from the inner facing surface a distance that ranges from about 0.001 inches to about 0.006 inches.

* * * * *